United States Patent [19]

Pollard

[11] Patent Number: 5,112,957
[45] Date of Patent: May 12, 1992

[54] METHOD AND APPARATUS FOR WASHING SOLID MEDIA

[76] Inventor: Harvey B. Pollard, 11008 Lamplighter La., Potomac, Md. 20854

[21] Appl. No.: 810,503

[22] Filed: Dec. 19, 1985

[51] Int. Cl.$^5$ .......................... C07K 3/00; C12M 3/00; B01D 24/46
[52] U.S. Cl. ................ 530/387.1; 530/412; 530/417; 530/350; 530/427; 435/284; 435/6; 435/7.1; 204/299 R; 210/772; 210/800; 536/27
[58] Field of Search ............. 530/427, 412, 417, 350, 530/387; 435/284; 204/299 R; 210/772, 800

[56] References Cited

U.S. PATENT DOCUMENTS 4,391,688  7/1983  Hamelin ..................... 204/299 R

OTHER PUBLICATIONS

Maniatis et al. "Molecular Cloning-a Laboratory Manual" Cold Spring Harbor Laboratory, 1982 pp. 383–386.

*Primary Examiner*—John Doll
*Assistant Examiner*—Abdel A. Mohamed
*Attorney, Agent, or Firm*—Larson and Taylor

[57] ABSTRACT

A method is described for safely and effectively washing solid gels or films containing biological macromolecules such as proteins or nucleic acids. The method involves placing the gels in an open plastic container and decanting a wash solution horizontally so as to leave the gel at the bottom of the container without using external means to hold the gel down. The undamaged gel can then be safely removed and detection experiments can thus be carried out. A preferred apparatus for carrying out this method is also described and consists of an elongated open-topped side spouted tray.

15 Claims, 2 Drawing Sheets

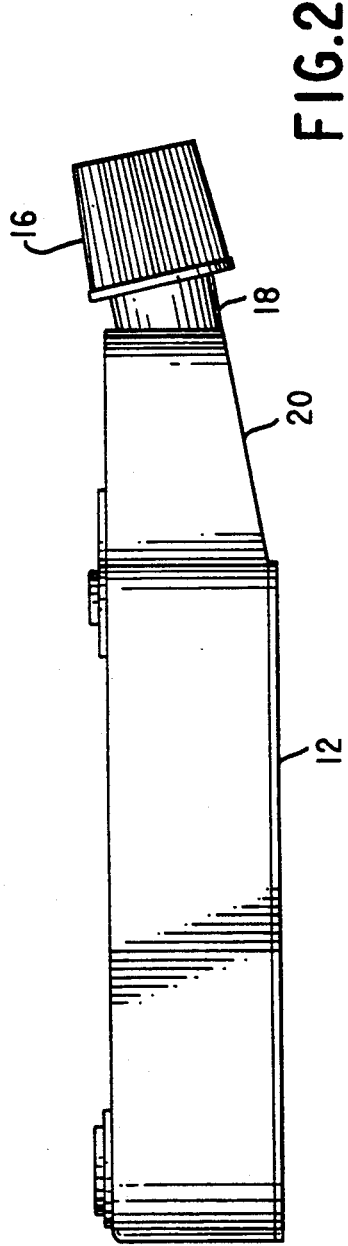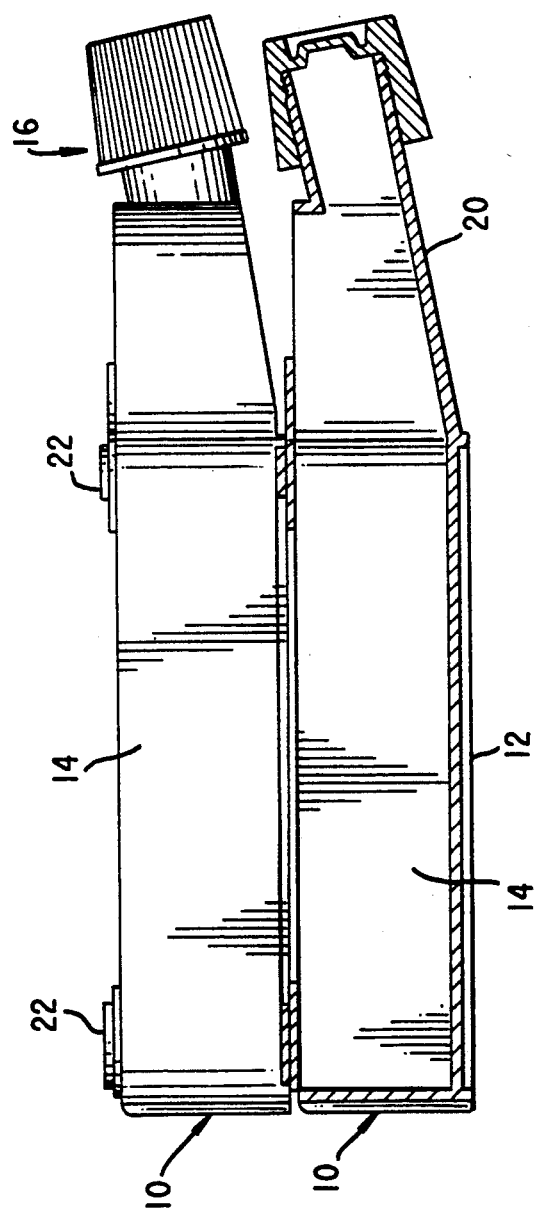

METHOD AND APPARATUS FOR WASHING SOLID MEDIA

FIELD OF THE INVENTION

This invention relates to a method for washing biological materials and an apparatus for carrying out the method.

BACKGROUND OF THE INVENTION

Specific protein, ligand, antibody and nucleic acid probes are used to detect macromolecules embedded in polyacrylamide or agarose gels, or attached to sheets of nitrocellulose or other related materials. However, prior to the detection step, extensive washing is often mandatory and the washing process often results in breakage of the sheets or gels. Further, these primitive washing procedures often lead to the wash solutions being splashed about, potentially causing contamination of the work bench or the scientist. Still further, the scientist often decants the wash solution while holding the solid media into the inverted tray by hand. This forces the scientist or lab assistant to have intimate contact with the solutions, some which are strongly radioactive (e.g. $^{125}I$, $^{32}P$, $^{35}S$, etc.) or carcinosenic. Mere use of gloves will seldom provide protection against these agents due to minor imperfections or tears in the glove surface. Additionally, the usual plastic gloves used in the lab are not radiation resistant. To avoid touching the medium that is being washed, a scientist can hold the materials in the tray with forceps; however, frequent handling with forceps often leads to marring or tearing of the gel or the strip.

It is thus desirable to have a system for washing biological materials which can overcome the above problems.

It is thus an object of the present invention to create a method for the safe and effective washing of biological materials which does not involve physically holding down the materials.

It is also an object of the present invention to provide an apparatus for carrying out the safe and effective washing of biological materials through the method of the present invention.

SUMMARY OF THE INVENTION

The present invention relates to a method of delicately washing biological or other macromolecules which avoids the need for physically holding these materials in place while a wash solution is being decanted.

The method of the present invention is particularly useful when the wash solutions used are potentially very harmful to the scientist. Through use of this method, a wash solution containing biological materials can be safely decanted, and the washed biological materials safely removed for further study without being marred or torn apart.

In carrying out the method of the present invention for washing biological or other macromolecules, a gel containing biological or other macromolecules is placed in a container, after which a wash solution is poured generally vertically onto the gel. The wash solution is then interacted with the macromolecules in the gel, after which the wash solution is decanted in a substantially horizontal direction, causing the wash solution to flow out of the container while concurrently causing the gel to adhere to the surface of the container and remain on that surface in the absence of external means to hold the gel down.

A side spouted, open-topped tray is particularly useful for carrying out this method. Using this apparatus to carry out the method of the present invention, one washes biological materials embedded in gels or films by first placing them at the bottom of the elongated, open-topped tray. The tray, which is preferably made of plastic, is then filled with a wash solution, and, after incubation, the solution is decanted through a spout on the side of the tray. The gel, which adheres to the bottom surface of the tray, remains behind following decantation, and can be removed safely and without damage for detection or further experimentation.

BRIEF DESCRIPTION OF THE DRAWINGS

There follows a detailed description of a preferred embodiment of the invention, which is to be read together with the accompanying drawings, wherein:

FIG. 2 is a side elevation view of the apparatus of FIG. 1.

FIG. 3 is a side elevation view of a stack of two of the trays of FIG. 1.

DETAILED DESCRIPTION OF THE INVENTION

Figure 1:
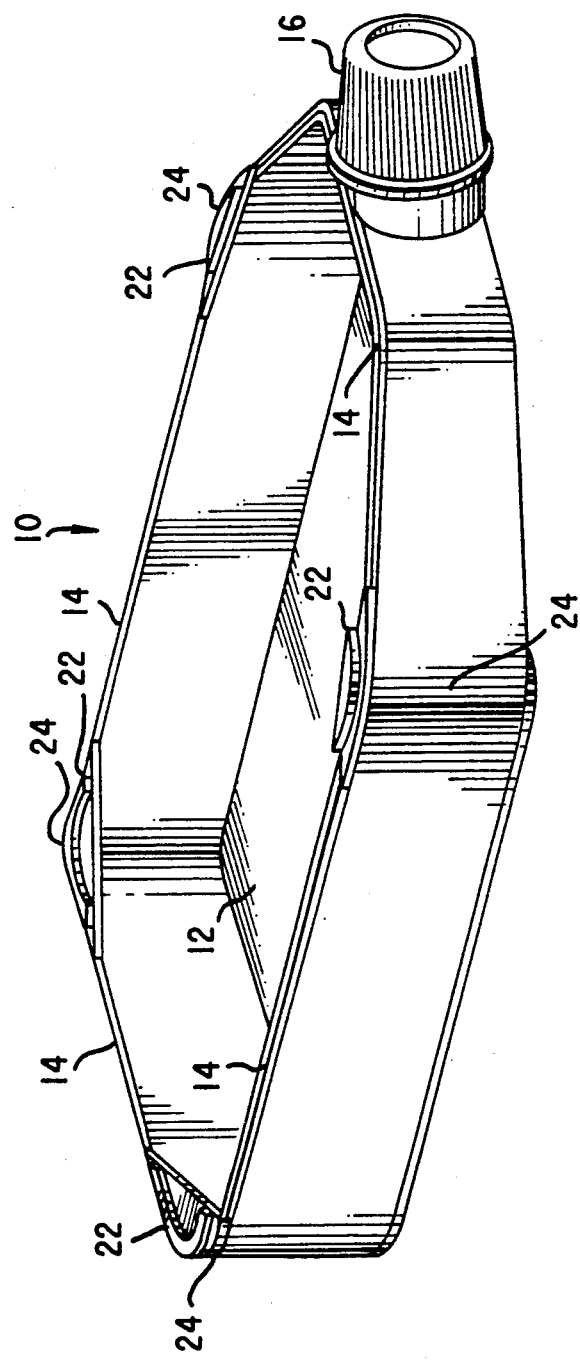
FIG. 1 is a perspective view of an apparatus for carrying out the method of the present invention.

The preferred apparatus for carrying out the method of the present invention, as observed in FIGS. 1-3, comprises a tray 10 with elongated flat bottom 12, side walls 14 integral with the bottom and forming a chamber capable of receiving and retaining a wash solution (not shown). The tray contains a spout 16 in one of the side walls, disposed so that the bottom 18 of the spout 16 lies flush with the bottom 12 of the tray 10. In the preferred embodiment, the bottom surface 12 of the tray is not totally flat, but rather has a forward end 20 which is slightly inclined upwards. This upward incline is helpful in retaining the biological media in the tray while the solution is decanted, as will be described in the description of the method below.

The tray can also include indented corners 22 which sit on top of the corners 24 of the tray 10. This allows the trays to be stacked if one desires to utilize or agitate several of the trays at one time. The stacked trays are observable in FIG. 3.

It is preferred that the tray be constructed of lucite or other related plastic material. The present invention takes advantage of the fact that gels of polyacrylamide or agarose, or nitrocellulose sheets and other similar materials have a physical affinity for these types of plastic surfaces. When solid media is slightly dried, it will tend to remain adhered to the flat bottom surface as the used solution flows away.

Although the invention can be constructed as specified above, it can also be made by modification of a conventional tissue culture flask. Such culture flasks are known in the art, and types of these flasks are observed in U.S. Pat. Nos. 4,334,028 and 3,870,602. The tray of the present invention can be constructed by removing the top face of the conventional tissue culture flask by any suitable means. Preferably, the top is removed so as to leave the indented corners 22 of the tray which allow stacking. This operation has been performed in two ways: (a) the face was removed by gently tapping with a hammer and removing pieces of broken plastic with a broad nosed pliers, and (b) cutting the upper face out with an electrically heated probe.

The tray, whether built from scratch, or made by altering a tissue culture flask, can be made in different sizes to accommodate different washing assignments. Trays have been made by modifying conventional tissue culture flasks which ranged from 75 cm² to 500 cm² surface area.

Once constructed, the open-topped spouted tray of the present invention is particularly useful in carrying out the safe and effective washing of biological materials using the method of the present invention. However, this is not the only tray which could be used, and many other suitable containers can be employed in the method of the present invention.

Using the apparatus described above, the preferred method of the present invention is as follows:

Gels or films containing macromolecules are placed into the tray directly from, e.g., an electrophoresis apparatus or a blot assembly. The tray is then filled with a wash solution until it is no more than half full. At this point the gel or film in the tray can be incubated with or without automatic agitation from a shaker. If agitation speed is moderate (about one cycle per second) the solution will remain in the tray without spillage. If faster agitation is desired, however, it is possible to seal the tray with parafilm or saran wrap, and this will prevent spillage.

Once incubated, the spout of the tray may be opened and the wash solution may be decanted. Due to the adherence of solid media to the plastic surface of the tray, and due to the upward incline at the spouted front end of the tray, the solid biological material embedded in the gel or sheet will remain at the bottom of the tray while the wash solution is removed through the spout. If desired, the entry from the tray chamber to the spout can be fitted with a vertical piece of plastic which will act as a meshwork at the point of exit for the solution. This allows one to handle and recover very thin pieces of nitrocellulose which might otherwise be washed away.

After this first decantation, it is possible to replenish the solution for further washes, or even change to a new solution when desired. When one has completed the washing, the biological media at the bottom of the tray can be removed in any suitable fashion. One way to remove the solid medium is by leaving the last wash solution undecanted, and then lifting out the materials using a plastic pancake turner. Alternatively, one can decant the solution as described above, and place a piece of dry filter paper or damp dialysis bag backing on the remaining gel or nitrocellulose strip. Then, removal can be accomplished simply by turning the tray over, and the protected solid media can be safely deposited in a suitable container or on another convenient surface.

As a result of this method, one obtains an undamaged sample of macromolecules in a sheet or a gel which is now ready for detection or further experimentation. Further, this unbroken sample is obtained without the contamination of lab or scientist which most often accompanied the prior art methods of washing these gelled biological materials.

Although the invention has been described in considerable detail, it will be apparent that numerous modifications and variations are possible, within the spirit and scope of the invention.

I claim:

1. A method of washing biological or other macromolecules comprising the steps of:
   (1) placing a gel, sheet or film containing biological or other macromolecules onto a surface within a container,
   (2) pouring a wash solution into the container onto said gel, sheet or film,
   (3) interacting the wash solution with the macromolecules in said gel, sheet or film, and
   (4) decanting said wash solution in a substantially horizontal direction which is generally parallel to said surface by slightly tipping the container at a small angle which is sufficient to cause said wash solution to flow out of said container in said direction, such that the washed gel, sheet or film remains within said container in the absence of external means to hold down said gel, sheet or film while said solution is being decanted.

2. A method of washing biological or other macromolecules as claimed in claim 1 wherein said container is incubated before decanting.

3. A method of washing biological or other macromolecules as claimed in claim 1 wherein said container is agitated before decanting.

4. A method of washing biological or other macromolecules as claimed in claim 3 wherein said container is sealed with a material selected from the group consisting of saran wrap and parafilm before agitation.

5. A method of washing biological or other macromolecules as claimed in claim 1 wherein said macromolecules comprises proteins, ligands, antibodies or nucleic acids.

6. A method of washing biological or other macromolecules as claimed in claim 1 wherein the macromolecules are contained by a gel and wherein said gel is comprises of polyacrylamide.

7. A method of washing biological or other macromolecules as claimed in claim 1 wherein the macromolecules are contained by a gel and wherein said gel is comprised of agarose.

8. A method of washing biological or other macromolecules as claimed in claim 1 wherein the macromolecules are contained by a sheet and wherein said sheet is comprised of nitrocellulose.

9. A method of washing biological or other macromolecules as claimed in claim 1 wherein said wash solution is filtered as it is being decanted.

10. A method of washing biological or other macromolecules as claimed in claim 1 wherein the container is comprised of a plastic.

11. A method of washing biological or other macromolecules as claimed in claim 10 wherein the container is comprised of lucite.

12. A method of washing and recovering biological or other macromolecules comprising the steps of:
   (1) placing a gel, sheet or film containing biological or other macromolecules onto a surface within a container,
   (2) pouring a wash solution into the container onto said gel, sheet or film,
   (3) interacting the wash solution with the macromolecules in said gel, sheet or film,
   (4) decanting said wash solution in a substantially horizontal direction which is generally parallel to said surface by slightly tipping the container at a small angle which is sufficient to cause said wash solution to flow out of said container in said direction such that the washed gel, sheet or film remains within said container in the absence of external means to hold down said gel, sheet of film while said solution is being decanted, and (5) removing the remaining gel, sheet or film with washed macromolecules from said container.

13. A method of washing and recovering biological or other macromolecules as claimed in claim 12 wherein said remaining gel, sheet or film is removed by lifting out said gel, sheet or film from said container with a pancake turner.

14. A method of washing and recovering biological or other macromolecules as claimed in claim 12 wherein said remaining gel, sheet or film is removed by placing a backing on the gel, sheet of film and turning the tray over to deposit the protected contents onto another surface.

15. A method of washing and recovering biological or other macromolecules as claimed in claim 14 wherein the backing is selected from the group consisting of dry filter bags and damp dialysis bags.

* * * * *